United States Patent [19]
Schumacher

[11] 3,957,890

[45] May 18, 1976

[54] PROCESS FOR THE NITRATION OF HALOAROMATICS

[75] Inventor: Ignatius Schumacher, St. Louis, Mo.

[73] Assignee: Monsanto Company, St. Louis, Mo.

[22] Filed: Aug. 20, 1973

[21] Appl. No.: 389,835

Related U.S. Application Data

[63] Continuation-in-part of Ser. No. 358,566, May 9, 1973.

[52] U.S. Cl. ............................................. 260/646
[51] Int. Cl.$^2$.......................................... G07C 79/12
[58] Field of Search .................................... 260/646

[56] References Cited
UNITED STATES PATENTS 3,140,319   7/1964   Sparks ............................... 260/646

*Primary Examiner*—Leland A. Sebastian
*Attorney, Agent, or Firm*—N. E. Willis; J. E. Maurer; F. D. Shearin

[57] ABSTRACT

It was found that the process for the nitration of halogenated aromatic compounds is improved by carrying out the nitration in the presence of a phosphorus compound in an amount sufficient to produce an ortho-directive effect. The addition of polyvalent metal elements such as vanadium, molybdenum, tungsten, and other elements that have the capability of existing in a variety of oxidation states, to a mixture of phosphoric and nitric acid improves the yield of the nitrohaloaromatics without affecting the isomer ratio.

9 Claims, No Drawings

PROCESS FOR THE NITRATION OF HALOAROMATICS

BACKGROUND OF THE INVENTION

This application is a continuation-in-part of application Ser. No. 358,566 filed May 9, 1973.

This invention relates to an improved process for the nitration of halogenated aromatic compounds whereby the ortho to para-isomer distribution is increased.

The present methods used in the nitration of halogenated aromatics, for example, the nitration of monochlorobenzene, yield a mixture of the para and ortho isomers, and place great emphasis on obtaining the para-isomer since it has, in the past, been in greater demand in the market. Nitrohalobenzenes are valuable chemical intermediates in the synthesis of dyes, photographic developers, anti-oxidants and gum inhibitors. Millions of pounds of these chemicals are produced each year to satisfy these needs.

As can be seen from a review of the prior art, the nitration of halobenzenes has been conducted under such conditions to maximize the para-isomer formation. As one example, U.S. Pat. No. 3,077,502 discloses that in the nitration of a halobenzene, a sulfonic acid and nitric acid mixture produces a para-directive effect. As another example, U.S. Pat. No. 3,140,319 teaches that the amount of para-isomer in a nitrohalobenzene nitration product can be increased by nitrating a halobenzene with a mixture of nitric acid and sulfuric acid.

Although the para-isomer of a nitrated haloaromatic is necessary for many industrial purposes, the ortho isomer is necessary for many other industrial uses, and market demands for the ortho and para-isomers have been changing. Flexibility in production is now necessary to meet increasing demands in the marketplace for the ortho isomer without a corresponding increase in the production of the para-isomer.

Previously, it was found that the para and ortho isomer distribution could be controlled without increasing the meta isomer formation, or the formation of dinitrated products, by nitrating a halobenzene in the presence of a phosphorus compound. The present invention improves the yield of the nitrated haloaromatic without affecting the isomer ratio.

SUMMARY OF THE INVENTION

It is an object of this invention to provide an improved process for the nitration of halogenated aromatic compounds. It is another object to provide an improved process for the nitration of halobenzenes. It is another object to provide an improved process particularly suitable for improving the yield of the nitrated haloaromatic without affecting the isomer ratio. It is another object to provide an improved process for preparing nitrochlorobenzene.

These and other objects are achieved in a process for the preparation of a nitro- and halo-substituted aromatic compound wherein a halogenated aromatic compound is contacted with a nitrating agent, the improvement which comprises carrying out the nitration in he presence of a phosphorus compound and a polyvalent metal element.

Broadly described, halogenated aromatic compounds are nitrated, according to the process of this invention, by contacting the halogenated aromatic compound with a nitrating agent at a temperature within the range of from about −30°C to about 160°C in the presence of a phosphorus compound and a polyvalent metal element. The para- to ortho-isomer ratio is controlled by the temperature of the reaction. The yield of the nitrated halo-aromatic compound is improved by the presence of the polyvalent metal elements.

The halogenated aromatics which can be employed in the process of this invention include: the monohalobenzenes, such as monochlorobenzene, monobromobenzene, monoiodobenzene and monofluorobenzene; the halonaphthalenes, such as chloronaphthalene, bromonaphthalene, iodonaphthalene and the like; dihalogenated benzenes, such as dichlorobenzene, dibromobenzene, chlorobromobenzene, difluorobenzene and the like. The process of this invention is particularly useful to nitrate monochlorobenzene.

Any nitrating agent which is capable of nitrating the nucleus of an aromatic compound can be used in the process of this invention, such as nitric acid, nitric anhydride, nitrogen tetroxide, ethyl nitrate and the like. Generally, the nitrating agent is employed in stoichiomtric quantities, or slightly in excess of the amount required to nitrate one site on the aromatic nucleus. Nitric acid is preferred.

Any number of phosphorus compounds can be used with the nitrating agent, according to the process of this invention, for the nitration of the halogenated aromatic compounds. Suitable phosphorus compounds include: phosphoric acids, such as metaphosphoric acid, orthophosphoric acid, triphosphoric acid, pyrophosphoric acid and the like; phosphorus oxides, such as phosphorus pentoxide and the like; phosphorus halides, such as phosphorus pentachloride, phosphorus trichloride, and the like; phosphorus oxyhalides, such as phosphorus oxychloride, phosphorus oxybromide, phosphorus oxyiodide and the like; phosphorous acids, such as orthophosphorous acid, metaphosphorous acid, pyrophosphorous acid and the like; and organophosphorus compounds, such as ethyl phosphate, methyl phosphate and the like. Phosphoric acids are preferred.

The process of this invention is not limited to specific reaction temperatures since the process can be carried out at temperatures of from about −30°C to temperatures of about 160°C or higher. A reaction temperature of −30°C can be maintained, for example, by employing a cooling bath comprising a slurry of solid carbon dioxide in acetone and using chloroform as a reaction diluent. However, those skilled in the art will recognize that the rate of reaction at temperatures of from about −30°C to 0°C will be somewhat slow. The minimum temperature for the process of this invention is, therefore, that temperature just above that at which no reaction between the nitrating agent and the haloaromatic compound will occur. The maximum temperature is only of economic importance for it is dependent upon economic factors rather than technical factors. For example, monochlorobenzene boils at about 130°C at sea level, and a pressurized reaction vessel is necessary at temperatures above 130°C. Temperatures within the range of from about 25° to about 130°C are desirably used, while temperatures within the range of from about 50° to about 90° C are preferred.

The specific reaction temperature used in the process of this invention affects the para to ortho isomer ratio. For example, when monochlorobenzene is nitrated at about 25°C using a mixture of nitric acid and phosphoric acid, the para to ortho isomer ratio is about 1.6:1; however, when the same reaction is carried out at about 100°C, the para to ortho isomer ratio is about 1.2:1.

Although the para to ortho isomer ratio can be controlled by the temperature of the reaction using a nitric acid-phosphoric acid mixture, the yield of nitrated haloaromatic product obtained by nitrating a haloaromatic compound is improved by the addition of compounds containing a polyvalent metal element to the acid mixture during the nitration. The term "polyvalent metal element" as used herein refers to those elements of the Periodic Table of the Elements which are metals and which have more than one valence state. Typical polyvalent metal elements include titanium, vanadium, chromium, manganese, iron, cobalt, nickel, copper, arsenic, selenium, niobium, molybdenum, ruthenium, rhodium, palladium, tin, antimony, tellurium, cerium, praseodymium, samarium, europium, erbium, thulium, ytterbium, tungsten, rhenium, osmium, iridium, platinum, gold, mercury, thallium, lead, bismuth, polonium, protactinium, uranium, and some of the transuranium elements. Molybdenum, manganese, vanadium, and tungsten are preferred, and molybdenum is especially preferred.

Any number of compounds can be used to add the polyvalent metal elements to the acid solution for the nitration reaction. It is only necessary that the polyvalent metal element is soluble, or at least partially soluble, in the acid solution. Salts of the polyvalent metal elements can be used such as the bromides, chlorides, iodides, fluorides, nitrates, oxylates, sulfates and the like. The polyvalent metal element can also be included as an anion, such as the titanate, vanadate, chromate, manganate, molybdate, tungstate, and the like. Furthermore, it is not important whether or not the polyvalent metal element is added to the acid solution in the lower or higher oxidation state, since the nitrating agent will generally oxidize the polyvalent metal element to the higher oxidation state. Compounds that contain two polyvalent metal elements, such as ferrimanganese citrate or ferric chromate can also be used The concentration of the polyvalent metal element in the reaction mixture can vary within broad ranges. As little as 250 parts per million by weight of the polyvalent metal element, based on the total weight of the reaction mixture, has been found to be effective, and as much as 2,500 parts per million by weight may be necessary when the reaction mixture contains more than about 10 weight percent water. When the acid contains about 10 weight percent water, it is preferred to use a concentration of polyvalent metal element between about 500 parts per million and about 1,500 parts per million by weight, and even more preferred to use a concentration of polyvalent metal element between about 750 and about 1,250 parts per million by weight.

The exact mechanism by which the polyvalent metal element improves the rate of nitration, and hence the yield of the nitrated haloaromatic compound, it not completely understood at this time. It is known, however, that when the phosphoric-nitric acid mixture contains about 10 percent water at the end of the nitration reaction, only about 70 percent yields are achieved, whereas when the polyvalent metal element is present in the acid mixture, yields of about 80 percent or more are achieved. As the concentration of water in the nitric acid-phosphoric acid mixture increases, the yield of nitrated haloaromatic decreases, but the effect of water on the yield is overcome when polyvalent metal elements are present in the acid mixture.

Although the prior art teaches that the presence of sulfuric or sulfonic acids are desirable to increase the rate of reaction between the nitrating agent and the haloaromatic compound, it has been found that sulfuric acid or sulfonic acids, even when present in small quantities, will not only change the isomeric ratio between the ortho and para isomer, but will also inhibit the rate of reaction when the polyvalent metal element is present. Thus, the use of sulfuric or sulfonic acids, even in small amounts, should be avoided in the process of this invention.

After the nitration reaction is complete, the product can be recovered from the nitration reaction mixture by any method well known to those skilled in the art. For example, the reaction mixture can be permitted to settle into two phases, i.e., an organic phase and an acid phase. The organic phase can be separated and the acid can be recovered for reuse or can be discarded. The specific isomers in the organic phase can be separated by any number of methods well known to those skilled in the art, for example, surface crystallization from the melt.

DESCRIPTION OF THE PREFERRED EMBODIMENTS

This invention is further illustrated by, but not limited to, the following examples:

EXAMPLES 1 - 5

To one mole of monochlorobenzene, one mole of phosphoric acid combined with 0.5 mole of nitric acid containing manganese chloride is added to the monochlorobenzene with vigorous stirring. The temperature is maintained between about 65° and 85°C, and the acid is added over a 1.5 hour period. After all of the acid has been added, the reaction mixture is maintained at a temperature between 65° and 85°C for 2 to 3 hours. The resulting mixture is permitted to separate into two phases and the bottom acid layer is drawn off. Analysis of the nitrochlorobenzene reaction product revealed that the para to ortho isomer ratio was about 1.37:1 in all cases. The results in Table I indicate the effect of the manganese chloride on the yield of nitrochlorobenzene. In all cases, the strength of the spent acid after the reaction was about 89%, indicating the presence of about 11% water. The percent conversion, shown in Table I, is expressed as a percentage of the conversion theoretically possible under these conditions since less than half of the nitric acid required to provide 100% nitrochlorobenzene was available in these examples to illustrate the effectiveness of this invention. The concentration of manganese is shown as the parts per million elemental manganese based on the weight of the monochlorobenzene nitric acid and phosphoric acid. Example 1, which does not contain any manganese, is given for comparison purposes to show the effect of the polyvalent metal element on the yield of nitrochlorobenzene.

TABLE I

| Example | Manganese Conc. (ppm) | Reactions Time (hrs) | Temp.(°C) | Percent Conversion |
|---|---|---|---|---|
| 1 | 0 | 2 | 70–75 | 70 |
| 2 | 400 | 2 | 70–75 | 80 |
| 3 | 1000 | 3 | 65–75 | 83 |
| 4 | 1000 | 3 | 75–80 | 93 |

TABLE I-continued

| Example | Manganese Conc. (ppm) | Reactions Time (hrs) | Temp.(°C) | Percent Conversion |
|---------|----------------------|---------------------|-----------|---------------------|
| 5 | 2000 | 3 | 80–85 | 92 |

EXAMPLE 6

To one mole of monochlorobenzene, one mole of nitric acid and two moles of phosphoric acid were slowly added with vigorous stirring. The acid solution contained 600 ppm by weight vanadium, based on the weight of the monochlorobenzene added as vanadium tetroxide. After all of the acid had been added, the reaction mixture was maintained at 70°C for 3 hours. Analysis of the nitrochlorobenzene reaction mixture indicated that the yield of nitrochlorobenzene was about 92%, and the para to ortho isomer ratio in the nitrochlorobenzene was about 1.42:1. The spent acid contained about 15% water.

EXAMPLE 7

The procedure of Example 6 was repeated except that 3,000 ppm molybdenum was added to the acid solution as ammonium molybdate. The yield of nitrochlorobenzene was about 93% and the para to ortho isomer ratio in the nitrochlorobenzene was about 1.32:1. The spent acid contained 8% water.

EXAMPLE 8

The procedure of Example 6 was repeated except that 1,000 ppm tungsten was added to the acid solution as tungstic acid. Analysis of the reaction mixture revealed that the yield of nitrochlorobenzene was about 93% and the para to ortho isomer ratio in the nitrochlorobenzene was about 1.31:1. The spent acid contained 8% water.

Although the invention has been described in terms of specified embodiments which are set forth in considerable detail, it should be understood that this is by way of illustration only and that the invention is not necessarily limited thereto, since alternative embodiments and operating techniques will become apparent to those skilled in the art in view of the disclosure. As an example, it can be seen that the spent acid can be washed with recycled monochlorobenzene to denitrify the acid, thus permitting the acid to be dehydrated or fortified and used in subsequent reactions without discarding. Accordingly, modifications are contemplated which can be made without departing from the spirit of the described invention.

What is claimed is:

1. In a process for the preparation of a nitro- and halo- substituted aromatic compound, wherein a halogenated aromatic compound is contacted with a nitrating agent, the improvement which comprises carrying out the nitration in the presence of a phosphorus compound and a polyvalent metal element.

2. In a process of claim 1 wherein the halogenated aromatic compound is a halobenzene.

3. In a process of claim 1 wherein the halobenzene is monochlorobenzene.

4. In a process of claim 1 wherein the phosphorus compound is phosphoric acid.

5. In a process of claim 1 wherein the polyvalent metal element is selected from the group consisting of molybdenum, manganese, vanadium and tungsten.

6. In a process of claim 1 wherein the polyvalent metal element is molybdenum.

7. In a process of claim 1 wherein the concentration of the polyvalent metal element is from about 250 to about 2,500 ppm by weight, based on the weight of the reaction mixture.

8. In a process of claim 7 wherein the concentration of the polyvalent metal element is from about 500 and about 1,500 ppm by weight, based on the weight of the reaction mixture.

9. In a process of claim 7 wherein the concentration of the polyvalent metal element is from about 750 to about 1,250 ppm by weight, based on the weight of the reaction mixture.

* * * * *